United States Patent

Armstrong et al.

Patent Number: 5,277,709
Date of Patent: Jan. 11, 1994

[54] COATING COMPOSITIONS

[75] Inventors: William P. Armstrong, Bolton; Emyr Phillips, Tingley, both of England

[73] Assignee: Ciba-Geigy Corporation, Ardsley, N.Y.

[21] Appl. No.: 822,446

[22] Filed: Jan. 16, 1992

[30] Foreign Application Priority Data

Jan. 23, 1991 [GB] United Kingdom ............... 9101468

[51] Int. Cl.$^5$ .............................................. C04B 9/02
[52] U.S. Cl. ............................... 106/1413; 106/14.15; 106/14.42; 106/14.18; 106/14.16; 524/288; 524/289; 524/98; 524/99; 252/392
[58] Field of Search .. 106/14.05–14, 42, 106/140S–42; 252/392; 524/98, 99, 104, 288, 289

[56] References Cited

U.S. PATENT DOCUMENTS

| | | | |
|---|---|---|---|
| 4,131,583 | 12/1978 | Boerwinkle | 260/296 HN |
| 4,366,076 | 12/1982 | Clark | 252/34 |
| 4,376,000 | 3/1983 | Lindert | 148/6.15 R |
| 4,400,365 | 8/1983 | Haacke et al. | 423/306 |
| 4,686,084 | 8/1987 | Geke et al. | 422/17 |
| 4,909,987 | 3/1990 | Penninger et al. | 422/17 |
| 5,128,396 | 7/1992 | O'Neil et al. | 524/288 |

FOREIGN PATENT DOCUMENTS

| | | |
|---|---|---|
| 0041927 | 12/1981 | European Pat. Off. |
| 0163107 | 12/1985 | European Pat. Off. |
| 0412933 | 2/1991 | European Pat. Off. |

OTHER PUBLICATIONS

S. Takenaka et al, J. Chem. Soc. Perkin Trans. II 1978, 95–99.
Derwent 87-119198/17 (Nippon Shashin INSA).

Primary Examiner—Mark L. Bell
Assistant Examiner—M. Einsmann
Attorney, Agent, or Firm—Luther A. R. Hall; William A. Teoli, Jr.

[57] ABSTRACT

A coating composition comprising a) an organic film-forming binder; and b) a corrosion-inhibiting amount of a substantially water-insoluble mono- or poly-basic salt of:

i) a ketoacid having the formula I:

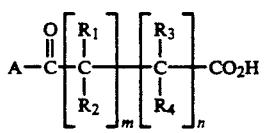

in which m and n, independently, are 0 or an integer from 1 to 10 provided that the sum of m and n is at least 1; A is $C_1$–$C_{15}$ alkyl, $C_2$–$C_{15}$ alkenyl, optionally substituted $C_3$–$C_{12}$ cycloalkyl, $C_2$–$C_{15}$ alkyl interrupted by one or more O-, N- or S-atoms, optionally substituted $C_6$–$C_{10}$ aryl, optionally substituted $C_7$–$C_{12}$ aralkyl, optionally substituted $C_7$–$C_{12}$ aralkenyl, a heterocyclic residue or a ferrocenyl residue; $R_1$, $R_2$, $R_3$ and $R_4$ are the same or different and each is a substituent A, hydrogen, OH, O-$C_1$–$C_{15}$ alkyl, $NH_2$, NH($C_1$–$C_{15}$ alkyl), N($C_1$–$C_{15}$ alkyl)$_2$, $CO_2H$, $CO_2$ ($C_1$–$C_{15}$ alkyl), $SO_3H$, P(O) (OH)$_2$ P(O)(OH)(O-$C_1$–$C_{15}$ alkyl), P(O) (O-$C_1$–$C_{15}$ alkyl)$_2$, SH, S($C_1$–$C_{15}$ alkyl), nitro, cyano, halogen or two of $R_1$, $R_2$ $R_3$ and $R_4$, together with the carbon atoms to which they are attached, form a $C_3$–$C_{12}$ cycloalkyl ring or $C_6$- or $C_{10}$ aryl ring, or one of $R_1$, $R_2$, $R_3$ and $R_4$ together with the carbon atom to which it is attached, and with the group A—C(=O)—, forms a ring, or $R_1$ and $R_2$, $R_3$ and $R_4$ form a carbonyl group or a C=C double bond, provided that A is not optionally substituted $C_6$–$C_{10}$ aryl when $R_1$, $R_2$, $R_3$ and $R_4$ are simultaneously hydrogen and provided that $R_1$ and $R_2$, or $R_3$ and $R_4$, respectively, are not simultaneously both OH or both $NH_2$; and ii) a base selected from a) a cation of Group Ia, Ib, IIa, IIb, IIIa, IIIb, IVa, IVb, Va, VIa, VIIa or VIIIa of the Periodic Table of Elements;

b) an amine of formula II which is specified herein.

23 Claims, No Drawings

COATING COMPOSITIONS

The present invention relates to coating compositions, in particular those containing, as corrosion inhibitors, certain metal or amine salts of ketoacids, as well as to those salts which are novel.

Protection against corrosion is one of the most important functions of organic coating compositions for metal substrates. Many suggestions for improving the protection of coatings against corrosion are to be found in the literature, for example in H. Kittel, Lehrbuch der Lacke und Beschichtungen ("Textbook of Paints and Coatings"), volume V, Stuttgart 1977, 46–103.

On the one hand, the barrier function of the coating composition can be improved, in order to keep corrosive agents, such as oxygen, water and ions, away from the metal surface. On the other hand, it is possible to employ corrosion-inhibiting pigments which intervene chemically or electrochemically in the corrosion process, for example by the formation of insoluble deposits with corrosion products or by passivation (polarisation) of the metal surface. Metal chromates and lead compounds rank amongst the most effective corrosion inhibiting pigments. Much use has been made of metal chromates, particularly because they inhibit both anodic and cathodic corrosion. Nowadays, there are are certain objections to the use of chromates owing to their potential carcinogenic action. Similarly, there are objections to the use of lead compounds owing to their chronic toxicity.

We have now found that certain metal or amine salts of ketoacids impart excellent corrosion inhibiting properties when incorporated into coating compositions.

Accordingly, the present invention provides coating compositions comprising
a) an organic film-forming binder; and
b) a corrosion-inhibiting amount of a substantially water-insoluble mono-or polybasic salt of i) a ketoacid having the formula (I):

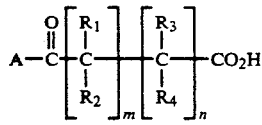

in which m and n, independently, are 0 or an integer from 1 to 10 provided that the sum of m and n is at least 1; A is $C_1$–$C_{15}$ alkyl, $C_2$–$C_{15}$ alkenyl, $C_3$–$C_{12}$ cycloalkyl, $C_2$–$C_{15}$ alkyl interrupted by one or more O-, N- or S-atoms, optionally substituted $C_6$–$C_{10}$ aryl, optionally substituted $C_7$–$C_{12}$ aralkyl, optionally substituted $C_7$–$C_{12}$ aralkenyl, a heterocyclic residue, or a ferrocenyl residue; $R_1$, $R_2$, $R_3$ and $R_4$ are the same or different and each is A, hydrogen, OH, O-$C_1$–$C_{15}$ alkyl, $NH_2$, NH($C_1$–$C_{15}$ alkyl), N($C_1$–$C_{15}$ alkyl)$_2$, $CO_2H$, $CO_2$-($C_1$–$C_{15}$ alkyl), $SO_3H$, P(O) (OH)$_2$, P(O)(OH(O-$C_1$–$C_{15}$ alkyl) P(O) (O-$C_1$–$C_{15}$ alkyl)$_2$, SH, S ($C_1$–$C_{15}$ alkyl), nitro, cyano, halogen, or two of $R_1$ to $R_4$, together with the carbon atoms to which they are bonded, may form a $C_3$–$C_{12}$ cycloalkyl ring or a $C_6$- or $C_{10}$ aryl ring, preferably a phenyl ring, or one of $R_1$ to $R_4$, together with the carbon atom to which it is attached, and with the group A—C(=O)— may form a ring, or $R_1$ and $R_2$, or $R_3$ and $R_4$ may form a carbonyl group or a C=C double bond, provided that A is not optionally substituted $C_6$–$C_{10}$ aryl when $R_1$, $R_2$, $R_3$ and $R_4$ are simultaneously hydrogen and provided that $R_1$ and $R_2$ or $R_3$ and $R_4$, respectively, are not simultaneous both OH or both $NH_2$ and ii) a base selected from a) a cation of group Ia, Ib, IIa, IIb, IIIa, IIIb, IVa, IVb, Va, VIa, VIIa or VIIIa of the Periodic Table of Elements; b) an amine of formula II:

in which X, Y and Z are the same or different and each is hydrogen, $C_1$–$C_{24}$ alkyl optionally interrupted by one or more O-atoms, phenyl, $C_7$–$C_9$ phenylalkyl, $C_7$–$C_9$ alkylphenyl, or two of X, Y and Z, together with the N-atom to which they are attached, form a 5-, 6- or 7-membered heterocyclic residue which optionally contains a further O-, N- or S- atom and which is optionally substituted by one or more $C_1$–$C_4$ alkyl, amino, hydroxy, carboxy or $C_1$–$C_4$ carboxyalkyl groups, and the other one of X, Y and Z is hydrogen, provided that X, Y and Z are not simultaneously hydrogen; c) a guanidine of formula R-N=C($NH_2$)$_2$ III in which R is hydrogen or $C_1$–$C_{15}$ alkyl and d) an amidine of formula R-C(=NH)$NH_2$ IV in which R is hydrogen or $C_1$–$C_{15}$ alkyl.

Optional ring substituents on aryl, aralkyl and aralkenyl groups A are halogen; nitro; cyano; $CF_3$; $C_1$–$C_{15}$ alkyl; $C_5$–$C_{12}$ cycloalkyl; $C_2$–$C_{15}$ alkenyl; $C_1$–$C_{12}$ halogenoalkyl; $C_1$–$C_{12}$ alkoxy; $C_1$–$C_{12}$ thioalkyl; $C_6$–$C_{12}$ aryl; $C_6$–$C_{10}$ aryloxy; $C_7$–$C_{12}$ alkaryl; $CO_2H$; $CO_2$-$C_1$–$C_{12}$ alkyl in which the alkyl group is optionally interrupted by one or more O-, N- or S-atoms; $CO_2$-$C_7$–$C_{12}$ alkaryl; $CO_2$-$C_6$–$C_{12}$ aryl in which the aryl group is optionally substituted with one or more carboxy groups; —C(=O)H; —C(=O)—$C_1$–$C_{12}$ alkyl in which the alkyl group is optionally interrupted by one or more O-, N- or S-atoms; —C(=O)—$C_7$–$C_{12}$ alkaryl; —C(=O)—$C_6$–$C_{12}$ aryl in which the aryl group is optionally substituted with one or more carboxy groups; $NH_2$; NH-$C_1$–$C_{15}$ alkyl or N($C_1$–$C_{15}$ alkyl)$_2$ in which the alkyl groups are optionally interrupted by one or more O-, N- or S-atoms.

$C_1$–$C_{15}$ Alkyl groups A, $R_1$, $R_2$, $R_3$ or $R_4$ may be straight or branched and include methyl, ethyl, n-propyl, isopropyl, n-butyl, t-butyl, n-pentyl, n-hexyl, n-octyl, n-decyl, n-dodecyl, n-tetradecyl and n-pentadecyl groups.

$C_2$–$C_{15}$ Alkenyl groups A, $R_1$, $R_2$, $R_3$ or $R_4$ include vinyl, 2-propenyl (allyl), but-1-en-3-yl, but-3-en-1-yl, (2-methyl)-prop-2-en-1-yl (isobutenyl), pent-1-enyl, (5-methyl) but-2-en-1-yl, hex-1-enyl, oct-1-enyl, dec-1-enyl, dodec-1-enyl and pentadec-1-enyl.

$C_3$–$C_{12}$ cycloalkyl groups A, $R_1$, $R_2$, $R_3$ or $R_4$ include cyclopropyl, cyclopentyl, cyclohexyl, cyclooctyl and cyclododecyl groups.

$C_2$–$C_{15}$ alkyl groups A, $R_1$, $R_2$, $R_3$ or $R_4$ which are interrupted by one or more O-, N- or S-atoms include methoxymethyl, ethoxymethyl, ethoxyethyl, 2-ethoxypropyl, 1-methoxybutyl, n-butoxymethyl, 1-methoxyoctyl, 1-methoxydecyl, 1-methoxypentadecyl, methylthiomethyl, ethylthiomethyl, ethylthioethyl, 2-ethylthiopropyl, 1-methylthiobutyl, n-butylthiomethyl, 1-methylthiododecyl, 1-methylthiopentadecyl, methylaminomethyl, ethylaminomethyl, ethylaminoethyl, 2-ethylaminopropyl, 1-methlaminodecyl and 1-methylaminopentadecyl.

$C_6-C_{10}$ Aryl groups A, $R_1$, $R_2$, $R_3$ or $R_4$ are naphthyl or, preferably, phenyl groups. Optional substitutents on such groups are e.g. chlorine or bromine atoms; nitro; cyano; $CF_3$; methyl, ethyl, n-propyl, isopropyl, n-butyl, t-butyl, n-hexyl, n-decyl, n-dodecyl or n-pentadecyl groups; cyclopentyl or cyclohexyl groups; vinyl, allyl, isobutenyl, hex-1-enyl, oct-1-enyl, dodec-1-enyl or pentadec-1-enyl groups; chloromethyl, chloroethyl, chlorobutyl, chlorohexyl, chlorodecyl, chloropentadecyl, bromomethyl, bromoethyl, bromopropyl, bromodecyl or bromopentadecyl groups; methoxy ethoxy, propoxy, butoxy, octoxy or dodecoxy groups; thiomethyl, thioethyl, thiopropyl, thiohexyl, or thiododecyl groups; thiophenyl groups; phenoxy groups; tolyl groups; carboxy groups; carboxymethyl, carboxyethyl, carboxydecyl, carboxypentadecyl, carboxymethoxymethyl, carboxymethylthiomethyl, carboxymethylaminomethyl groups, carboxymethylphenyl or carboxy-phenyl, carboxy (4-carboxyphenyl), carboxy (4-acetylphenyl) or carboxy (4-aminophenyl) groups.

Heterocyclic residues A include, e.g. pyridyl, furyl, thiophenyl and pyrrolyl residues.

When one or more of $R_1$, $R_2$, $R_3$ and $R_4$ is a group $O-C_1-C_{15}$ alkyl, examples of such groups include methoxy, ethoxy, propoxy, butoxy, octoxy, decoxy, and pentadecoxy groups, examples of groups $-NH(C_1-C_{15}$ alkyl) and $N-(C_1-C_{15}$ alkyl)$_2$ are methylamino, dimethylamino, ethylamino, diethylamino and dipentadecylamino groups; examples of groups $-CO_2(-C_1-C_{15}$ alkyl) include methylcarboxy, ethylcarboxy, decylcarboxy and pentadecylcarboxy groups; examples of groups $P(O)(OH)(O-C_1-C_{15}$ alkyl) are methyl phosphonate, ethyl phosphonate and pentadecyl phosphonate, of $P(O) (O-C_1-C_{15}$ alkyl)$_2$ are dimethyl phosphonate, diethyl phosphonate and dipentadecyl phosphonate groups; and examples of groups $S-(C_1-C_{15}$ alkyl) are methylthio, ethylthio, decylthio and pentadecyl thio groups.

With respect to the base, component ii) of the salts b) used in the compositions of the present invention, cation bases include sodium, potassium and lithium (Group 1A), copper, silver and gold (Group IB); magnesium, calcium, strontium and barium (Group IIA); zinc, cadmium and mercury (Group IIB); scandium and yttrium (Group IIIA); aluminium (Group IIIB); titanium and zirconium (Group IVA); tin and lead (Group IVB); vanadium (Group VA); chromium, molybdenum and tungsten (Group VIA); manganese (Group VIIA); and cobalt (Group VIIIA), using the IUPAC 1970 Periodic Table convention.

When the base component ii) of the salts b), is an amine of formula II:

II $C_1-C_{24}$ alkyl radicals X, Y and Z, include methyl, ethyl, n-propyl, iso-propyl, n-butyl, n-hexyl, n-octyl, n-decyl, n-tetradecyl, n-eicosyl and tetraeicosyl radicals. $C_4-C_{24}$ alkyl radicals X, Y and Z which are interrupted by one or more oxygen atoms include, e.g. 2-ethoxypropyl, 1-methoxybutyl, n-butoxymethyl, 1-methoxyoctyl, 1-methoxydecyl, 1-methoxydodecyl, 1-methoxyhexadecyl, 1-methoxyeicosyl, 1-methoxytetraeicosyl and 2-methoxyethoxymethyl. $C_7-C_9$ phenylalkyl groups X, Y and Z are, e.g., benzyl, 1-phenylethyl, 2-phenylethyl, alpha-methylbenzyl, alpha, alpha-dimethylbenzyl or 3-phenylpropyl. $C_7-C_9$ Alkylphenyl groups X, Y and Z include, e.g., tolyl, xylyl, ethylphenyl and propylphenyl. Heterocyclic groups formed by two of X, Y and Z are preferably saturated heterocyclic groups, especially 6-membered saturated heterocyclic groups such as piperidino, morpholino, thiomorpholino, piperazino or 4-($C_1-C_4$ alkyl)-piperazino groups.

Guanidine base components ii) of salts b) include guanidine, methylguanidine, ethylguanidine, n-butylguanidine, n-octylguanidine, n-decylguanidine and n-pentadecylguanidine.

Amidine base components ii) of salts b) include amidine, methylamidine, ethylamidine, n-butylamidine, n-hexylamidine, n-octylamidine, n-decylamidine and n-pentadecylamidine.

Alkyl, alkenyl, halogenoalkyl, alkoxy, thioalkyl, carboxyalkyl, alkylcarbonyl or alkylamino-carbonyl groups A, $R_1$, $R_2$, $R_3$ or $R_4$, preferably contain up to 4 carbon atoms. When a group A, $R_1$, $R_2$, $R_3$ or $R_4$ is interrupted by an atom, or is substituted by a substituent group, preferably one or two of such interrupting atoms or substituent groups are present.

Preferred groups A are $C_1-C_{15}$ alkyl, $C_2-C_{15}$ alkenyl, $C_1-C_{15}$ alkyl optionally interrupted by one O-, N- or S-atom, $C_5-C_{10}$ cycloalkyl or $C_6$- or $C_{10}$ aryl each optionally substituted by one or two halogen, nitro, cyano, $CF_3$, $C_1-C_4$ alkyl, $C_5-C_6$ cycloalkyl, $C_2-C_4$ alkenyl, $C_1-C_4$ halogenoalkyl, $C_1-C_4$ alkoxy, $C_1-C_4$ thioalkyl, phenyl, phenoxy, $C_1-C_4$ alkylphenyl, carboxy, carboxy-$C_1-C_4$ alkyl, $C_1-C_4$ alkylcarbonyl, $C_1-C_4$ alkylaminocarbonyl or di ($C_1-C_4$ alkyl) aminocarbonyl groups.

More preferably, A is $C_6$ or $C_{10}$ aryl, $C_4-C_{10}$ alkyl or $C_5-C_{10}$ cycloalkyl, each optionally substituted with one or more halogen atoms, in particular a chlorine or fluorine atom which is preferably in the 4-position when A is phenyl; $C_1-C_3$ alkyl groups; or $C_1-C_3$ alkoxy groups.

$R_1$, $R_2$, $R_3$ and $R_4$ are preferably hydrogen or a group which has been indicated as a preferred group A. Preferably $R_3$ and $R_4$ are hydrogen.

Preferably m+n is an integer ranging from 2 to 8, especially 2, 3 or 4.

Preferred metal cations ii) a) are Mg, Ca, Ba, Ti, Mn, Fe, Co, Ni, Cu, Zn, Zr and Mo.

Preferred amines ii b) are primary $C_8-C_{14}$ alkylamines which preferably have branching at the alpha C-atom of the alkyl chain.

The ketoacids of formula I and the amines of formula II are known compounds, and many are available commercially. In German Offenlegungsschrift 3338953, ketoacids of formula:

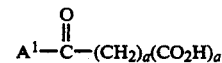

in which $A^1$ is optionally substituted phenyl and a is 2 or 3 are described, along with related compounds. This German patent specification indicates that the disclosed ketoacids, or their water-soluble alkali-, ammonium-, ammonia- or alkanolamine salts, are useful as corrosion inhibitors in aqueous systems, e.g. in detergents, coolants, hydraulic fluids, or cooling waters.

No hint is given that the disclosed ketoacids, or the specified salts, could find use in specific aqueous systems such as paints. No mention is made of water-insoluble metal or amine salts of said ketoacids.

Specific examples of ketoacids of formula (I) are 2-benzoyl cyclopropane carboxylic acid, 2-benzoyl; 3-(2-thenoyl)propionic acid; 3-(2-pyridoyl) propionic acid; 1,2,3-Dihydro-3-oxo 1H indene-1-carboxylic acid; 3-(4-methylbenzoyl)-2-methyl propionic acid; 3-(4-methyl benzoyl)-3-methyl propionic acid; 4-(4-methyl benzoyl)-3-carboxy-butanoic acid; 3-(benzoyl)-2-hydroxy-propanoic acid; 3-(4-methylbenzoyl)-2-bromo-propanoic acid; 3-(2-furoyl)-propanoic acid; 4-oxo cyclohexane butanoic acid; 4-oxo-decanoic acid; 1,2,3,4-tetrahydro-1-oxo-2-naphthalene acetic acid; benzoyl butanedioic acid-1-ethyl ester; 2-(4-methyl benzoyl)-1-carboxy-ethyl phosphonic acid; $\alpha,\epsilon$-dioxo-benzene hexanoic acid; cis-2-(4-methyl benzoyl)-cyclohexane carboxylic acid; 4-oxo-hex-5-enoic acid; and 2-benzoyl benzoic acid.

The water-insoluble metal salt component b) of coating compositions of the invention may be prepared by adding an appropriate soluble metal ion, in aqueous solution, to an aqueous solution of an alkali metal salt of the ketoacid; and then filtering off the precipitated metal salt.

The water-insoluble amine salt component b) of the coating composition of the invention may be prepared by heating a ketoacid of formula I and an amine of formula II, or a guanidine or amidine carbonate, at 30°-130° C., preferably 50°-60° C., optionally in a solvent e.g. methanol, xylene or tetrahydrofuran.

The water-insoluble salts derived from a ketoacid of formula I an amine of formula II or a guanidine of formula III or an amidine of formula IV are new and are a further object of this invention. Preferred compounds and substituents are the same as described above in the compositions of this invention.

The organic film-forming binder component a) of the coating compositions of the present invention may be any film-former suitable for solvent-based, but in particular for aqueous-based coating compositions. Examples of such film-forming binders are epoxide resins, polyurethane resins, aminoplast resins or mixtures of such resins; or a basic aqueous dispersion, or solution of an acidic resin.

Of particular interest are organic film-forming binders for aqueous-based coating compositions e.g. alkyd resins; acrylic resins; two-pack epoxy resins; polyester resins which are usually saturated; water-dilutable phenolic resins or dispersions thereof; water-dilutable urea resins; and vinyl/acrylic copolymer resins.

More specifically, the alkyd resins may be water-dilutable alkyds such as air-drying or bake systems which may be used in combination with water-dilutable melamine resins; or alkyd emulsions either oxidatively- or air-drying or bake systems, optionally used in combination with water-borne acrylics or copolymers thereof, vinyl acetates etc.

Acrylic resins may be straight acrylics; acrylic acid ester copolymers; combinations or copolymers with vinyl resins e.g. vinyl acetate, or with styrene. These systems may be air-drying or bake systems.

Water-dilutable epoxide resins, in combination with suitable polyamine curing agents have good mechanical and chemical stability. By the polyaddition of epoxide resin with amine, thermosets are obtained having very high film hardness. The addition of organic solvents is not necessary when liquid epoxy-based resins are used for aqueous systems.

When using epoxide-solid resin dispersions, a minor amount of solvent is necessary for improved film formation.

Preferred epoxide resins are those based on aromatic polyols, in particular bisphenols. The epoxide resins are used in conjunction with a curing agent. The latter can be, in particular, an amino or hydroxy compound or an acid or an acid anhydride or a Lewis acid. Examples of these are polyamines, polyaminoamides, polysulfide polymers, polyphenols, boron fluoride and complexes thereof, polycarboxylic acids, 1,2-dicarboxylic acid anhydrides or pyromellitic dianhydride.

In addition to the components a) and b), the coating compositions of the invention can also contain further components, for example pigments, dyes, extenders and other additives such as are customary for coating compositions. The pigments can be organic, inorganic or metallic pigments, for example titanium dioxide, iron oxide, aluminium bronze, phthalocyanine blue etc. It is also possible to use concomitantly anti-corrosion pigments, for example pigments containing phosphates or borates, metal pigments and metal oxide pigments (see Farbe und Lack 88 (1982,183) or the pigments described in European Patent A 54,267. Examples of extenders which can be used concomitantly are talc, chalk, alumina, barytes, mica or silica. Examples of further additives are flow control auxiliaries, dispersing agents, thixotropic agents, adhesion promoters, antioxidants, light stabilisers or curing catalysts.

Particular importance attaches to the addition of basic extenders or pigments. In certain binder systems, for example in acrylic and alkyd resins, these produce a synergistic effect on the inhibition of corrosion. Examples or such basic extenders or pigments are calcium carbonate, magnesium carbonate, zinc oxide, zinc carbonate, zinc phosphate, magnesium oxide, aluminium oxide, aluminium phosphate or mixtures thereof. Examples of pigments are those based on aminoanthraquinone.

Finally, the corrosion inhibitor can also be applied to a neutral carrier. Suitable carriers are, in particular, pulverulent extenders or pigments. This technique is described in greater detail in German Offenlegungsschrift 3,122,907.

In addition to the component b), the coating composition can also contain another organic, metal-organic or inorganic corrosion inhibitors, for example salts of nitroisophthalic acid, tannin, phosphoric esters, technical amines, substituted benzotriazoles or substituted phenols, such as are described in German Offenlegungsschrift 3,146,262.

The coating compositions according to the invention are preferably used as a primer on metallic substrates, in particular on iron, steel, copper, aluminium, aluminium alloys or zinc. Here they can function as so-called conversion coatings, in that chemical reactions take place at the interface between the metal and the coating. The application of the coatings can be effected by the customary methods, such as spraying, brushing, roller coating, powder coating, dipping or electrodeposition, in particular cathodic deposition. Depending on whether the film-former is a resin which dries physically or can be cured by heat or radiation, the curing of the coatings is carried out at room temperature, by stoving or by irradiation.

The corrosion inhibitors can be added to the coating composition during the preparation of the latter, for example during the distribution of the pigment by grinding. The inhibitor is used in an amount of 0.01–20% by weight, preferably 0.5–5% by weight, based on the solids content of the coating composition.

Recently, there has been an increased commercial interest in the production of surface coatings by electrodeposition viz. the deposition of a film-forming material under the influence of an applied electrical potential. Various coating materials have been developed for this method of application, but the technique is often associated with various disadvantages. In particular, it is difficult to attain desired levels of corrosion inhibition using this method of applying surface coatings.

We have now found that the water-insoluble salt component b) of the coating compositions of the present invention imparts excellent corrosive-inhibiting properties to both cathodic and anodic electrocoats.

As component a) of the electrodepositable cathodic aqueous coating compositions of the present invention, there may be used e.g. and epoxy resin optionally cross-linked with a capped or blocked organic polyisocyanate; acrylic resins optionally and preferably crosslinked with a capped or blocked isocyanate; acrylic or other unsaturated resins crosslinked via double bonds; adducts of epoxy resins with amines, polycarboxylic acids or their anhydrides or aminocarboxylic, mercaptocarboxylic or aminosulphonic acids; polyurethanes; polyesters; and reaction products of phenolic hydroxyl group-containing resins with an aldehyde and an amine or amino- or mercapto-carboxylic or aminosulphonic acid; as well as mixtures of these resins.

Preferred adducts of an epoxide resin with an amine are adducts of a polyglycidyl ether, which may be of a polyhydric phenol or a polyhydric alcohol, with a monoamine. Suitable polyglycidyl ethers include those of dihydric alcohols such as butane-1,4-diol, neopentyl glycol, hexamethylene glycol, oxyalkylene glycols and polyoxyalkylene glycols, and tri-hydric alcohols such as glycerol, 1,1,1-trimethylolpropane and adducts of these alcohols with ethylene oxide or propylene oxide. It will be understood by those skilled in the art that these polyglycidyl ethers of polyhydric alcohols are usually advanced, i.e. converted into longer chain higher molecular weight polyglycidyl ethers, for example by reaction with a dihydric alcohol or phenol, so that the resulting polyglycidyl ethers given adducts with suitable electrodepositable film-forming properties on reaction with the secondary monoamine. Preferred polyglycidyl ethers are those of polyhydric phenols, including bisphenols such as bisphenol F, bisphenol A and tetrabromobisphenol A and phenolic novolak resins such as phenol-formaldehyde or cresol-formaldehyde novolak resins. These polyglycidyl ethers of phenols may have been advanced, for example by reaction with dihydric alcohols or phenols such as those hereinbefore described. Particularly preferred polyglycidyl ethers are polyglycidyl ethers of bisphenol A advanced by reaction with bisphenol A.

Monoamines suitable for adduct formation with the polyglycidyl ethers include primary, secondary or tertiary amines. Secondary amines are preferred e.g. dialkylamines such as diethylamine, di-n-propylamine, di-isopropylamine, di-n-butylamine, di-n-octylamine and di-n-dodecylamine or nitrogen heterocycles such as piperidine or morpholine.

Preferred secondary monoamines are secondary alkanolamines such as diethanolamine, N-methylethanolamine, N-butylethanolamine, diisopropanolamine, N-methylisopropanol-amine or di-n-butanolamine. A particularly preferred secondary alkanolamine is diethanolamine.

Thus preferred adducts of polyglycidyl ether with a secondary monoamine are adducts of a polyglycidyl ether of a polyhydric phenol, which may have been advanced, with secondary alkanolamine, while particularly preferred such adducts are those of a polyglycidyl ether of bisphenol A, advanced by reaction with bisphenol A, with diethanolamine.

Electrodeposition of the organic resin may be carried out using conventional procedures. The pigments can be organic, inorganic or metallic pigments, for example titanium dioxide, iron oxide, aluminium bronze, phthalocyanine blue etc. It is also possible to use concomitantly anti-corrosion pigments, for example pigments containing phosphates or borates, metal pigments and metal oxide pigments (see Farbe and Lack 88 (1982), 183) or the pigments described in European Patent 54,267.

The corrosion inhibitor component b) may be added to the electrodepositable coating system during the preparation of the latter, for example, during the distribution of the pigment by grinding e.g. by the methods disclosed in EP 107089. Alternatively, the corrosion inhibitors can be incorporated into the non-emulsified resins and also into the grind resin. The corrosion inhibitors are preferably used in an amount of 0.01 to 20% by weight, preferably 0.05 to 5% by weight, based on the solids content of the electrodepositable coating composition.

Electrodeposition for only a few minutes, usually one minute, at a voltage of up to 500 volts is sufficient in most cases. Usually, voltage programs, viz stepwise increase of the voltage, are used.

The coating compositions of the present invention may be applied to any electrically conductive substrate especially metals such as iron; steel; e.g. cold-rolled steel, optionally treated with zinc phosphate or galvanized; copper; zinc; and aluminium; more especially zinc or aluminium alloys.

After electrodeposition of the organic resin film, the substrate is rinsed with de-mineralized water, air-blated and baked at elevated temperature e.g. up to 500° F.

This invention also comprises a method of applying a coating composition according to the present invention as a primer coating on metal substrates, in particular on iron, steel, copper, aluminium, aluminium alloys or zinc, thereby producing an organic, corrosion-resistant surface coating on a corrodable metal surface, comprising treating the corrodable metal surface with a composition according to this invention, then drying or curing the coating composition to produce a dried or cured surface coating on the metal surface.

The following Examples further illustrate the present invention. Examples 1 to 3 relates to the production of known acid precursors useful in the production of new salts according to the present invention.

EXAMPLE 1

4-Tolualdehyde (39.6 g, 0.33 mol) and 2M NaOH solution (230 ml) are added to a solution of levulinic acid (39.5 g, 0.34 mol) in EtOH (85 ml) over 1 hour. The resulting clear solution is poured into ice and acidified with 6M HCl. The resulting gum obtained is crystallised with acetone/water and recrystallised from $CH_2Cl_2$ to yield 14.0 g of 6-(4 methylphenyl)-4-oxo-hex-5-enoic acid as colourless crystals m.p. 129–130.

Calculated: C, 71.5; H, 6.5 Found: C, 71.2; H, 6.4.

EXAMPLE 2

Aluminium trichloride (50.7 g, 0.38 mol) is added, portionwise, over 15 min, to a solution of methylsuccinic anhydride (20 g, 0.175 mol), toluene (32.3 g, 0.35 mol) and nitrobenzene (100 ml). The reaction mixture is stirred for 3 hours and then warmed to 80° C. for half an hour. On cooling, it is quenched with water (75 ml) and then conc HCl (30 ml). The solid ppt. is filtered, dissolved in $Na_2CO_3$ solution, washed with $CH_2Cl_2$, reacidified and the product filtered to yield 23.4 g of 3-(4-methylbenzoyl)-2-methyl-propionic acid as a white solid, m.p. 168°–170°.

Calculated: C, 69.9; H, 6.8 Found: C, 68.9; H, 7.0.

EXAMPLE 3

Triethylamine (10.1 g, 0.1 mol) is added to a solution of heptanal (11.4 g, 0.1 mol), acrylonitrile (5.31 g, 0.1 mol) and 3-benzyl-5-(2-hydroxyethyl)-4-methylthiazolium chloride (2.69 g, 0.01 mol) and the mixture stirred for 8 hours. The mixture is poured into 1% $H_2SO_4$ (150 ml) and extracted with $CHCl_3$ (4×50 ml). This extract is washed with water, $NaCO_3$ solution, and dried over $NaSO_4$ to yield a brown oil. After distillation, (bp 150–175/0.08 mbar), the colourless oil obtained (9.5 g) is hydrolysed with 2.5M NaOH (100 ml) to yield 4.5 g of 4-oxodecanoic acid as a pale brown semi-solid.

Calculated: C, 64.5; H, 9.7 Found: C, 63.7; H, 9.8.

EXAMPLE 4

6-(4-methylphenyl)-4-oxo-hex-5-enoic acid (15.9 g; 0.073 mol) is dissolved in tetrahydrofuran (100 mls) and treated with t-tridecylamine (14.5 g, 0.073 mol). The resulting solution is evaporated to give 30.4 g of t-tridecylammonium 6-(4-methylphenyl)-4-oxo-hex-5-enoate, as a pale yellow oil.

EXAMPLES 5–11

In a manner similar to that described in Example 4, further salts are prepared as summarised in Table 1. Yields are quantitative in every case.

TABLE 1

| EXAMPLE | KETO ACID | AMINE | FORM | ANALYSIS REQUIRES | FOUND | 1H NMR δ |
|---|---|---|---|---|---|---|
| 4 | $CH_3$—C$_6$H$_4$—CH=CH—C(O)—CH$_2$CH$_2$—CO$_2$H | $^tC_{13}H_{27}NH_2$ | Pale Yellow Oil | C 74.8 H 10.4 N 3.4 | 74.5 10.9 3.6 | 8.6–6.8, m, 8H; 6.5, d, 1H; 3.0–2.4, m, 4H; 2.4, S, 3H; 1.8–0.8, m, 27H |
| 5 | $CH_3$—C$_6$H$_4$—C(O)—CH$_2$—CH(CH$_3$)—CO$_2$H | $^tC_{13}H_{27}NH_2$ | Pale Yellow Oil | C 74.2 H 10.4 N 3.5 | 72.9 10.9 3.7 | 8.3–7.3, m, 7H; 4.1–2.8, m, 3H; 2.62, S, 3H; 2.2–0.8, m, 30H |
| 6 | n-$C_6H_{13}$—C(O)—CH$_2$CH$_2$—CO$_2$H | $^tC_{13}H_{27}NH_2$ | Pale Yellow Oil | C 71.6 H 12.3 N 3.6 | 70.5 12.5 3.7 | 6.2, brs, 3H; 2.5–2.0, m, 6H; 1.6–0.7, m, 38H; |
| 7 | $CH_3$—C$_6$H$_4$—C(O)—CH$_2$—CH(Ph)—CO$_2$H | $^tC_{13}H_{27}NH_2$ | Pale Yellow Oil | C 77.0 H 9.7 N 3.0 | 75.3 9.9 4.0 | 8.0–6.7, m, 12H; 4.1–2.8, m, 3H; 2.2, s, 3H; 1.8–0.8, 27H; |
| 8 | Ph—C(O)—C$_6$H$_4$—CO$_2$H | $^tC_{13}H_{27}NH_2$ | Pale Yellow Oil | C 76.4 H 9.0 N 3.3 | 75.0 9.7 3.4 | 8.2–7.0, m, 12H; 1.8–0.8, 27H |
| 9 | thienyl—C(O)—CH$_2$CH$_2$—CO$_2$H | $^tC_{13}H_{27}NH_2$ | Pale Yellow Oil | C 65.8 H 9.7 N 3.6 | 65.1 10.0 3.6 | 7.7–7.4, m, 5H; 7.0, dd, 1H; 3.2, t, 2H; 2.6, t, 2H; 1.8–0.8, m, 27H |
| 10 | $CH_3$—C$_6$H$_4$—C(O)—CH$_2$—CH(CO$_2$H)—CH$_2$—CO$_2$H | $2.^tC_{13}H_{27}NH_2$ | Pale Yellow Oil | C 72.2 H 11.2 N 4.3 | 70.2 11.4 4.3 | 8.0–7.1, m, 7H; 3.4–2.6, m, 5H; 2.3, s, 3H, 1.8–0.8, 54H |

TABLE 1-continued

| EXAMPLE | KETO ACID | AMINE | FORM | ANALYSIS REQUIRES | FOUND | 1H NMR δ |
|---|---|---|---|---|---|---|
| 11 | 4-oxo-2,3-dihydro-1H-indene-1-carboxylic acid | $^tC_{13}H_{27}NH_2$ | Pale Yellow Oil | C 73.7<br>H 9.3<br>N 3.7 | 72.6<br>10.0<br>4.9 | 7.6–6.9, m, 10H;<br>3.9, m, 1H; 3.3–2.3,<br>m, 2H; 1.8–0.8,<br>m, 27H; |
| 12 | trans-2-(4-methylphenyl)cyclohexane-1-carboxylic acid | $^tC_{13}H_{27}NH_2$ | Semi Solid | C 75.5<br>H 10.6<br>N 3.1 | 74.6<br>11.1<br>3.1 | 8.0–7.0, m, 7H;<br>4.0, m, 1H;<br>2.4, S, 3H;<br>2.2–0.8, m, 36H |
| 13 | cis-2-(4-methylphenyl)cyclohexane-1-carboxylic acid | $^tC_{13}H_{27}NH_2$ | Semi Solid | C 75.5<br>H 10.6<br>N 3.1 | 73.8<br>10.7<br>3.2 | 8.0–7.0, m, 7H;<br>3.7, m, 1H;<br>3.0–0.8, m, 39H |
| 14 | 3-methyl-4-oxo-4-phenylbutanoic acid | $^tC_{13}H_{27}NH_2$ | Pale Yellow Oil | C 73.6<br>H 10.6<br>N 3.6 | 71.3<br>10.9<br>3.8 | 8.1–7.2, m, 8H;<br>4.0, m, 1H;<br>3.0–2.0, m, 2H;<br>1.8–0.8, m, 30H |
| 15 | 4-ferrocenyl-4-oxobutanoic acid | $^tC_{13}H_{27}NH_2$ | Black Oil | C 66.8<br>H 8.9<br>N 2.9 | 65.5<br>10.7<br>2.9 | 6.8, brs, 3H;<br>4.8, t, 2H; 4.5, t, 2H;<br>4.2, S, 5H; 3.0<br>m.2H, 2.5, m, 2H. |
| 16 | 4-cyclohexyl-4-oxobutanoic acid | $^tC_{13}H_{27}NH_2$ | Pale Yellow Oil | C 72.0<br>H 11.8<br>N 3.7 | 71.7<br>12.1<br>4.0 | 7.1, brs, 3H;<br>3.0–0.8m, 42H,<br>1.8–0.8, m, 27H |
| 17 | 4-(4-methylphenyl)-4-oxo-3-(4-methylphenyl)butanoic acid | $^tC_{13}H_{27}NH_2$ | Pale Yellow Oil | C 77.3<br>H 9.9<br>N 2.9 | 75.8<br>10.0<br>2.9 | 8.2–7.0, m, 11H;<br>4.0–3.0, m, 3H;<br>2.3, s, 3H; 2.2, s, 3H;<br>1.8–0.8, m, 27H |
| 18 | 2-(ethoxycarbonyl)-4-oxo-4-phenylbutanoic acid | $^tC_{13}H_{27}NH_2$ | Pale Yellow Oil | C 69.4<br>H 9.6<br>N 3.1 | 68.0<br>9.7<br>3.1 | 8.2–7.2, m, 8H;<br>4.7, t, 1H; 4.1, q, 2H;<br>2.8, dd, 2H;<br>1.8–0.6, m, 30H |
| 19 | 4-oxo-4-(pyridin-2-yl)butanoic acid | $^tC_{13}H_{27}NH_2$ | Brown Oil | C 69.8<br>H 10.1<br>N 7.4 | 68.2<br>10.1<br>7.4 | 8.7, m, 1H; 8.2–7.4,<br>m, 6H; 3.6, t, 2H;<br>2.7, t, 2H;<br>1.8–0.8, m, 27H |
| 20 | 2-phosphono-4-(4-methylphenyl)-4-oxobutanoic acid | $2.^tC_{13}H_{27}NH_2$ | Semi Solid | C 66.2<br>H 10.7<br>N 4.2 | 61.2<br>11.1<br>4.3 | 8.2–7.2, m, 10H;<br>3.7–3.0, m, 2H;<br>2.6–2.4, m, 4H;<br>1.8–0.8, m, 54; |

TABLE 1-continued

| EXAMPLE | KETO ACID | AMINE | FORM | ANALYSIS REQUIRES | FOUND | 1H NMR δ |
|---|---|---|---|---|---|---|
| 21 | O=C-CH₂-CH₂-CO₂H with CO₂H branch | 2.$^i$C$_{13}$H$_{27}$NH$_2$ | Glass | C 69.2<br>H 11.9<br>N 4.9 | 67.9<br>11.9<br>4.9 | 6.0, brs, 6H;<br>2.3, m, 8H;<br>1.8–0.8, m, 54H; |
| 22 | Ph-C(=O)-CH₂-CH(OH)-CO₂H | $^i$C$_{13}$H$_{27}$NH$_2$ | Pale Yellow Oil | C 70.4<br>H 9.8<br>N 3.6 | 73.3<br>9.9<br>4.1 | 8.2–7.3, m, 5H;<br>5.5, brs, 4H, 3.8–3.0<br>m, 3H; 1.8–0.8, m, 27H |

EXAMPLES 23–52

An aqueous alkaline paint formulation having a solids content of 56.15 wt %, is prepared using the following formulation.

60.03 wt % Bayhydrol B (alkyd resin 30% in water)
0.14 wt % Servosyn WEB (8%; cobalt drier)
0.28 wt % Ascinin v (aliphatic oxime)
18.18 wt % Bayferrox 130M (micronised red iron oxide)
5.15 wt % Heladol 10 (surfactant)
10.6 wt % micronised talc
0.2 wt % Aerosil 300 (silica-based thixotropic agent)
0.9 wt % butylglycol
0.05 wt % aluminium octoate
0.46 wt % water
1.12 wt % (2% by weight on solids content) of a product of Examples 4 to 22 is dispersed in separate samples of the paint formulation.

Each paint sample is applied on to cold rolled steel plates at a layer thickness of 55–60 microns and dried for 72 hours at 20° C.

The painted plates incorporating product from Examples 4 to 22 are scribed and then placed in a sealed chamber and exposed to condensed moisture for 840 hours at 40° C./100% relative humidity. (Followed by NaOH treatment as below*)

The results are summarised in Table 2.

The painted plates incorporating the product from Examples 4, 5, 6, 10 and 12, 14 to 18 and 20 to 22 are scribed and subjected to a saltspray test procedure (168 hours) as specified in ASTM B117. At the end of the test, the coating is removed by treatment with conc. *NaOH solution and the corrosion of the metal at the cross-cut (as specified in NIN 53,167) and at the remainder of the surface is assured. In every case, the assessment is made on the basis of a 6-stage scale.

The corrosion Protection Factor, CPF is given by the sum at the assessment at the coating and metal surface. The higher the value the more effective the inhibitor under test.

The results are summarised in Table 3.

TABLE 2

HUMIDITY RESULTS

| Example | Additive | % Additive | Assessment of coating | Assessment of metal | CPF |
|---|---|---|---|---|---|
| — | Control | 0 | 3.6 | 0.6 | 4.2 |
| 23 | Product of Example 6 | 2 | 5.4 | 5.3 | 10.7 |
| 24 | Product of Example 7 | 2 | 4.8 | 2.6 | 7.4 |
| 25 | Product of Example 8 | 2 | 5.4 | 4.6 | 10.0 |
| 26 | Product of Example 9 | 2 | 4.4 | 4.0 | 8.4 |
| 27 | Product of Example 10 | 1 | 6.0 | 5.0 | 11.0 |
| 28 | Product of Example 11 | 2 | 4.0 | 5.5 | 9.5 |
| 29 | Product of Example 12 | 2 | 2.8 | 2.0 | 4.8 |
| 30 | Product of Example 13 | 2 | 4.9 | 4.3 | 9.2 |
| 31 | Product of Example 14 | 1 | 4.4 | 2.3 | 6.7 |
| 32 | Product of Example 15 | 2 | 3.6 | 2.6 | 6.2 |
| 33 | Product of Example 16 | 2 | 6.0 | 3.0 | 9.0 |
| 34 | Product of Example 17 | 2 | 5.6 | 3.6 | 9.2 |
| 35 | Product of Example 18 | 2 | 6.0 | 2.7 | 8.7 |
| 36 | Product of Example 19 | 2 | 4.2 | 3.5 | 7.7 |
| 37 | Product of Example 20 | 2 | 6.0 | 3.6 | 9.6 |
| 38 | Product of Example 21 | 1 | 3.2 | 1.3 | 4.5 |
| 39 | Product of Example 22 | 2 | 4.8 | 3.8 | 8.6 |

TABLE 3

SALT SPRAY RESULTS

| Example | Additive | % Additives | Assessment of coating | Assessment of metal | CPF |
|---|---|---|---|---|---|
| — | Control | 0 | 2.8 | 0.6 | 3.4 |
| 40 | Product of Example 4 | 2 | 4.0 | 2.7 | 6.7 |
| 41 | Product of Example 5 | 2 | 3.6 | 0.6 | 4.2 |
| 42 | Product of Example 6 | 2 | 2.6 | 3.0 | 5.6 |
| 43 | Product of Example 10 | 2 | 4.0 | 2.0 | 6.0 |
| 44 | Product of Example 12 | 2 | 3.0 | 1.6 | 4.6 |
| 45 | Product of Example 14 | 2 | 2.0 | 1.6 | 3.6 |
| 46 | Product of Example 15 | 1 | 3.2 | 1.3 | 4.5 |
| 47 | Product of Example 16 | 2 | 3.0 | 2.6 | 5.6 |
| 48 | Product of Example 17 | 2 | 2.6 | 1.3 | 3.9 |
| 49 | Product of Example 18 | 2 | 2.0 | 2.0 | 4.0 |
| 50 | Product of Example 20 | 2 | 4.6 | 3.1 | 7.7 |
| 51 | Product of Example 21 | 1 | 3.2 | 1.3 | 4.5 |
| 52 | Product of | 2 | 2.8 | 1.3 | 4.1 |

TABLE 3-continued

SALT SPRAY RESULTS

| Example | Additive | % Additives | Assessment of coating | Assessment of metal | CPF |
|---------|----------|-------------|----------------------|--------------------|-----|
| Example 22 | | | | | |

We claim:

1. A coating composition comprising A) an organic film-forming binder; and B) a corrosion-inhibiting amount of a substantially water-insoluble mono- or poly-basic salt of:
   i) a ketoacid having the formula I:

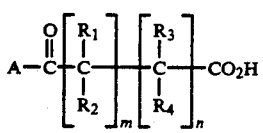

in which m and n, independently, are 0 or an integer from 1 to 10 provided that the sum of m and n is at least 1; A is $C_1$-$C_{15}$alkyl, $C_2$-$C_{15}$alkenyl, optionally substituted $C_3$-$C_{12}$cycloalkyl, $C_2$-$C_{15}$alkyl interrupted by one or more O-, N- or S-atoms, optionally substituted phenyl ($C_1$-$C_6$)alkylene optionally substituted $C_7$-$C_{12}$aralkenyl, a heterocyclic residue or a ferrocenyl residue; $R_1$, $R_2$, $R_3$ and $R_4$ are the same or different and each is a substituent A, hydrogen, OH, O-$C_1$-$C_{15}$alkyl, $NH_2$, $NH(C_1$-$C_{15}$alkyl), $N(C_1$-$C_{15}$alkyl)$_2$, $CO_2H$, $CO_2$($C_1$-$C_{15}$alkyl), $SO_3H$, $P(O)$ $(OH)_2$ $P(O)(OH)(O$-$C_1$-$C_{15}$alkyl) $P(O)$ $(O$-$C_1$-$C_{15}$alkyl)$_2$, SH, $S(C_1$-$C_{15}$alkyl), nitro, cyano, halogen or two of $R_1$, $R_2$, $R_3$ and $R_4$, together with the carbon atoms to which they are attached, form a $C_3$-$C_{12}$cycloalkyl ring or $C_6$- or $C_{10}$aryl ring, or one of $R_1$, $R_2$, $R_3$ and $R_4$ together with the carbon atom to which it is attached, and with the group A—C(=O)—, forms a ring, or $R_1$ and $R_2$, or $R_3$ and $R_4$ form a carbonyl group or a C=C double bond, provided that $R_1$ and $R_2$, or $R_3$ and $R_4$, respectively, are not simultaneously both OH or both $NH_2$; and
   ii) a base selected from
      a) a cation of Group I, Ib, IIa, IIb, IIIa, IIIb, IVa, IVb, Va, VIa, VIIa or VIIIa of the Periodic Table of Elements;
      b) an amine of formula II:

in which X, Y and Z are the same or different and each is hydrogen, $C_1$-$C_{24}$alkyl optionally interrupted by one or more O-atoms, phenyl, $C_7$-$C_9$phenylalkyl, $C_7$-$C_9$alkylphenyl, or two or X, Y and Z, together with the N-atom to which they are attached form a 5-, 6- or 7-membered heterocyclic residue which optionally contains a further O-, N- or S-atom, and which is optionally substituted by one or more $C_1$-$C_4$alkyl, amino, hydroxy, carboxy or $C_1$-$C_4$carboxy alkyl groups, and the other one of X, Y and Z is hydrogen, provided that X, Y and Z are not simultaneously hydrogen;
      c) a guanidine of formula R-N=C(NH$_2$)$_2$ in which R is hydrogen or $C_1$-$C_{15}$alkyl; and
      d) an amidine of formula R-C(=NH)NH$_2$ in which R is hydrogen or $C_1$-$C_{15}$alkyl.

2. A composition according to claim 1 in which A is $C_1$-$C_{15}$ alkyl, $C_2$-$C_{15}$ alkenyl, $C_1$-$C_{15}$ alkyl optionally interrupted by one O-, N- or S-atom, $C_5$-$C_{10}$ cycloalkyl optionally substituted by one or two halogen, nitro, cyano, $CF_3$, $C_1$-$C_4$ alkyl, $C_5$-$C_6$ cycloalkyl, $C_2$-$C_4$ alkenyl, $C_1$-$C_4$ halogenoalkyl, $C_1$-$C_4$ alkoxy, $C_1$-$C_4$ thioalkyl, phenyl, phenoxy, $C_1$-$C_4$ alkylphenyl, carboxy, carboxy-$C_1$-$C_4$ alkyl, $C_1$-$C_4$ alkylcarbonyl, $C_1$-$C_4$ alkylaminocarbonyl or di-($C_1$-$C_4$ alkyl) aminocarbonyl groups.

3. A composition according to claim 2 in which A is $C_5$-$C_{10}$ cycloalkyl or $C_4$-$C_{10}$ alkyl, each optionally substituted by one or more halogen atoms or $C_1$-$C_3$ alkyl or $C_1$-$C_3$ alkoxy groups.

4. A composition according to claim 3 in which the halogen substituent is chlorine or fluorine.

5. A composition according to claim 1 in which $R_1$, $R_2$, $R_3$ and $R_4$ are hydrogen or $C_1$-$C_{15}$ alkyl, $C_2$-$C_{15}$ alkenyl, $C_1$-$C_{15}$ alkyl optionally interrupted by one O-, N- or S-atom, $C_5$-$C_{10}$ cycloalkyl or $C_6$- or $C_{10}$ aryl each optionally interrupted by one or two halogen, nitro, cyano, $CF_3$, $C_1$-$C_4$ alkyl, $C_5$-$C_6$ cycloalkyl, $C_2$-$C_4$ alkenyl, $C_1$-$C_4$ halogenoalkyl, $C_1$-$C_4$ alkoxy, $C_1$-$C_4$ thioalkyl, phenyl, phenoxy, $C_1$-$C_4$ alkylphenyl, carboxy, carboxy-$C_1$-$C_4$ alkyl, $C_1$-$C_4$ alkylcarbonyl, $C_1$-$C_4$ alkylaminocarbonyl or di($C_1$-$C_4$ alkyl) aminocarbonyl groups.

6. A composition according to claim 5 in which $R_1$, $R_2$, $R_3$ and $R_4$ are hydrogen or $C_6$-$C_{10}$ aryl, $C_5$-$C_{10}$ cycloalkyl or $C_4$-$C_{10}$ alkyl, each optionally substituted by one or more halogen atoms or $C_1$-$C_3$ alkyl or $C_1$-$C_3$ alkoxy groups.

7. A composition according to claim 6 in which the halogen substituent is chlorine or fluorine.

8. A composition according to claim 7 in which $R_1$, $R_2$, $R_3$ and $R_4$ are hydrogen or phenyl having a chlorine or fluorine atom in the 4-position of the phenyl ring.

9. A composition according to claim 1 in which $R_3$ and $R_4$ are each hydrogen.

10. A composition according to claim 1 in which the sum of m and n is an integer ranging from 2 to 8.

11. A composition according to claim 10 in which the sum of m and n is 2, 3 or 4.

12. A composition according to claim 1 in which the base ii) is Mg, Ca, Ba, Ti, Mn, Fe, Co, Ni, Cu, Zn, Zr or Mo.

13. A composition according to any of claim 1 in which the base ii) is a primary $C_8$-$C_{14}$ alkylamine.

14. A composition according to claim 13 in which the amine has branching at the alpha carbon atom of the alkyl chain.

15. A composition according to claim 1 in which the organic film-forming binder component a) is an epoxy resin, a polyurethane resin, an aminoplast resin, an acrylic resin, an acrylic copolymer, a polyvinyl resin, a phenolic resin, a styrene-butadiene copolymer, a polyester resin, an alkyl resin, a mixture of such resins, or an aqueous basic or acid dispersion of such resins, or an aqueous emulsion of such resins.

16. A composition according to claim 15 in which the epoxy resin is one based on aromatic polyols.

17. A composition according to claim 15 in which the acrylic polymer is a vinyl acrylic polymer or a styrene acrylic polymer.

18. A composition according to claim 1 in which there are present, in addition to components a) and b), one or more of a pigment, dye, extender and other conventional coating composition additives.

19. A composition according to claim 18 in which a basic extender or pigment is present.

20. A composition according to claim 1 in which a further organic, metal-organic or inorganic corrosion inhibitor is present.

21. A composition according to claim 1 in which component b) is present in an amount ranging from 0.01 to 20% by weight, based on the solids content of the coating compositions.

22. A coating composition according to claim 1, in which the organic film-forming binder is aqueous and electrodepositable.

23. A composition according to claim 22 in which the binder a) is an acrylic polymer, a polybutadiene copolymer or an adduct of an epoxide resin with an amine.

* * * * *